(12) United States Patent
Buckland et al.

(10) Patent No.: US 8,999,366 B2
(45) Date of Patent: *Apr. 7, 2015

(54) POROUS BIOMATERIAL ON HYDROXYAPATITE

(75) Inventors: Thomas Buckland, Aylesbury (GB); Charles Campion, Barnet (GB)

(73) Assignee: ApaTech Limited, Elstree, Hertfordshire (GB)

( * ) Notice: Subject to any disclaimer, the term of this patent is extended or adjusted under 35 U.S.C. 154(b) by 401 days.

This patent is subject to a terminal disclaimer.

(21) Appl. No.: 12/865,573

(22) PCT Filed: Feb. 2, 2009

(86) PCT No.: PCT/GB2009/000308
§ 371 (c)(1),
(2), (4) Date: Nov. 15, 2010

(87) PCT Pub. No.: WO2009/095703
PCT Pub. Date: Aug. 6, 2009

(65) Prior Publication Data
US 2011/0059151 A1  Mar. 10, 2011

(51) Int. Cl.
*A61F 2/00* (2006.01)
*A61K 33/42* (2006.01)
*C01B 15/16* (2006.01)
*A61L 27/56* (2006.01)
*A61L 27/12* (2006.01)
*A61F 2/28* (2006.01)

(52) U.S. Cl.
CPC ............. *A61L 27/56* (2013.01); *A61L 27/12* (2013.01); *A61F 2/28* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 6,302,913 B1 | 10/2001 | Ripamonti et al. | |
| 6,511,510 B1 | 1/2003 | de Bruijn et al. | |
| 2002/0165616 A1 | 11/2002 | Heide et al. | |
| 2004/0078087 A1 | 4/2004 | Kim et al. | |
| 2006/0110422 A1 | 5/2006 | Tas et al. | |
| 2007/0218098 A1 | 9/2007 | Reif et al. | |

FOREIGN PATENT DOCUMENTS

| | | |
|---|---|---|
| DE | 29922585 | 7/2000 |
| DE | 29922585 U1 | 7/2000 |
| EP | 1449818 A1 | 8/2004 |
| EP | 1584338 A2 | 10/2005 |
| EP | 0951441 B1 | 7/2006 |
| EP | 1829564 | 9/2007 |
| GB | 2142919 | 1/1985 |
| WO | 9628117 | 9/1996 |
| WO | 00/20353 A1 | 4/2000 |
| WO | 00/42991 A1 | 7/2000 |
| WO | 0062829 | 10/2000 |
| WO | 2006082442 | 8/2006 |
| WO | 2006/115398 A1 | 11/2006 |
| WO | 2007094672 | 8/2007 |
| WO | 2007/124511 A2 | 11/2007 |

OTHER PUBLICATIONS

Liu, Dean Mo, Fabrication of Hydroxyapatite ceramic with controlled porosity, Journal of Material Science: Material in Medicine, 8 (1997), pp. 227-232.*
Habiboic, et al., "3D microenvironment as essential element for osteainduction by biomaterials," Biomaterials 26 (2005) 3565-3575.
Ferraz, et al., "Effect of chemical composition on hydrophobicity and zeta potential of plasma sprayed HA/CaO- P2O5 glass coatings," Biomaterials 22 (2001) 3105-3112.
Klucakova, "Analysis of relationship between properties and behaviour of materials used and impregnation conditions of carbon-carbon composites," Acta Materialia 53 (2005) 3841-3848.
Lopes, et al., "Hydrophobicity, surface tension, and zeta potential measurements of glass-reinforced hydroxyapatite composites," J. Biomed. Mat., vol. 45, Issue 4, pp. 370-375, Jun. 15, 1999.
Habiboic, et al., "Relevance of Osteoinductive Biomaterials in Critical-Sized Orthotopic Defect," Journal of Orthopaedic Research May 2006, 24 (5). pp. 867-876.
Yamasaki, et al., "Osteogenic response to porous hydroxyapatite ceramics under the skin of dogs," Biomaterials vol. 13, Issue 5, 1992, pp. 308-312.
Kwon, et al., "Synthesis and dissolution behavior of (β-TCP and HA/β-TCP composite powders," Journal of the European Ceramic Society 23 (2003) 1039-1045.
GB Search Report dated May 29, 2008 issued in related Application No. GB0801935.8 (2 pages).
International Search Report and Written Opinion dated Apr. 7, 2009 issued in related International Patent Application No. PCT/GB2009/000296.
Search Report issued Jun. 25, 2009 in related application No. GB0800335.2 (1 page).
International Search Report (6 pages) and Written Opinion of the ISA (7 pages) issued Apr. 7, 2009 in related application No. PCT/GB2009/000308.
Office Action dated Jan. 24, 2013 issued in related U.S. Appl. No. 12/865,633, 12 pgs.

* cited by examiner

*Primary Examiner* — Scott Long
*Assistant Examiner* — Lyndsey Beckhardt
(74) *Attorney, Agent, or Firm* — Bret E. Field; Bozicevic, Field & Francis LLP

(57) ABSTRACT

The present invention provides a synthetic non-resorbable silicon-containing calcium phosphate biomaterial having a microporosity of 23% by volume or greater, wherein the surface free energy of the biomaterial is 19 mJ/m.

16 Claims, 1 Drawing Sheet

POROUS BIOMATERIAL ON HYDROXYAPATITE

The present invention relates to an osteoinductive biomaterial. More particularly, the present invention relates to a silicon-containing calcium phosphate material having a defined pore structure.

BACKGROUND TO THE INVENTION

When a bone-replacement material is implanted in patient, the formation of living bone may be induced at the surface of the bone. This is termed osteoconduction. In addition, living bone may in certain circumstances form within the material itself, penetrating the structure of the bone-replacement material. This is termed osteoinduction.

When osteoinduction occurs, bone is formed at a non-bony (i.e. ectopic) site. Osteoinduction is thought to be beneficial because, over time, the growth of bone penetrating a material can result in the more resilient integration of the bone-replacement material into already existing bone at, for example, the site of an osseous defect. However, many osteoconductive biomaterials do not exhibit osteoinduction.

Osteoinduction is promoted and/or accelerated by osteoinductive materials. In other words, osteoinductive materials are capable of inducing bone growth and the formation of bone in non-osseous tissue. When implanted in patients, osteoinductive materials are of significant therapeutic value because they promote and accelerate bone growth. For example in patients with compromised bone biology, the promotion and acceleration of bone repair can lead to shorter fracture-repair times and a lower incidence of non-unions or pseudo-arthroses.

To date, the most popular way of achieving osteoinduction in a biomaterial has been to include powerful cytokine proteins in a therapeutic form. The best known and most widely used of these proteins are the Bone Morphogenetic Proteins (BMP), particularly BMP-2 and BMP-7. These have been provided as recombinant human proteins (as present for example in the 'InFuse'® and 'OP-1' bone replacement materials currently on the market), or as gels, powders or fibres derived from highly processed cadaver human bone and generically referred to as Demineralised Bone Matrix (DBM).

The disadvantages of using these proteins are well-known. While Bone Morphogenetic Protein products are certainly effective in their ability to promote rapid bone growth in preclinical studies, the use of recombinant human Bone Morphogenetic Protein products can also result in significant negative side-effects, such as uncontrolled bone resorption, runaway bone formation and, from a financial viewpoint, extremely high costs per therapeutic unit. Numerous clinical adverse events have been recorded using these highly-potent therapies, some resulting in major harm to patients. The mechanisms behind the occurrence of these adverse events are not currently well-understood.

In addition, the performance of products derived from Demineralised Bone Matrix is known to be highly variable and very donor-dependant. One solution to this would be to batch mix products from different donors. However, as all Demineralised Bone Matrix products have to maintain lot traceability, batch mixing is not possible. In addition, the levels of Bone Morphogenetic Proteins (from which the Demineralised Bone Matrix's osteoinductive properties are thought to derive) are very low and below established therapeutic thresholds for predictable, repeatable performance. As a result of these drawbacks, Demineralised Bone Matrix products have not demonstrated equivalent performance to current, commonly-used therapies in other equivalent orthopaedic and neurosurgical fields.

Another disadvantage of conventional Bone Morphogenetic Protein products is that they are not localised to a persistent scaffold which supports bone growth. Specifically, Bone Morphogenetic Protein products are typically provided as liquids which have to be adsorbed onto suboptimal scaffolds. The unpredictability of the absorption process can result in insufficient adsorption of the proteins, followed by implant compression and extrusion of the active agent into nerve spaces, causing severe harm or disability once bone formation has eventually been induced.

An alternative approach to relying on intentionally-introduced Bone Morphogenetic Proteins to provide osteoinductive activity is to provide a material having intrinsic osteoinductivity. The material is typically a scaffold material that itself promotes and accelerates bone growth without having to be treated with Bone Morphogenetic Proteins before being implanted into a patient.

One approach to, provide an osteoinductive material has been to select a material that is resorbable. For example, the dissolution of calcium and phosphate from a calcium phosphate material are thought by some to be the key to providing an osteoinductive material. This approach is extended in, for example, PCT/NL2006/000210, which suggests that the dissolution of certain trace elements from a calcium phosphate material further promotes osteoinduction.

Another example of material that is claimed to have intrinsic osteoinductivity is described in U.S. Pat. No. 6,302,913. This material is "bioinert", but, according to U.S. Pat. No. 6,302,913, has a surface geometry with a series of concavities that is said to concentrate Bone Morphogenetic Proteins absorbed from circulatory fluid in order to induce bone formation. However, these types of materials have also not yet resulted in strong in vivo promotion of bone growth.

As a result of at least some of the drawbacks with the prior art, the inventors of the present invention have set about to provide a material having intrinsic osteoinductivity but without relying on the sometimes unpredictable dissolution of trace elements or manipulation of surface geometry to provide osteoinduction.

EP 0951441 describes the synthesis of a dense silicon-substituted hydroxyapatite material.

SUMMARY OF THE INVENTION

The present invention provides a synthetic non-resorbable silicon-containing calcium phosphate biomaterial having a microporosity of 23% by volume or greater, wherein the surface free energy of the biomaterial is 19 mJ/m$^2$ or greater.

The present invention further provides a synthetic non-resorbable silicon-containing calcium phosphate biomaterial having a microporosity of 23% by volume or greater. The present invention further provides a silicon-containing sintered calcium phosphate biomaterial having a microporosity of 23% by volume or greater. The present invention further provides a synthetic silicon-substituted calcium phosphate biomaterial having a microporosity of 23% by volume or greater, wherein biomaterial comprises substantially no impurity phases of calcium oxide and/or tricalcium phosphate.

The present invention further provides a synthetic calcium phosphate biomaterial as defined herein for use in medicine. The present invention further provides a method of treating bone fractures, achieving spinal fusions, repairing bone tumours or vertebral compression fractures, the method comprising implanting a biomaterial as defined herein in a patient or animal.

The present invention further provides a method of selecting a synthetic porous osteoinductive biomaterial and providing osteoinduction of bone, the method comprising: (a) selecting an osteoinductive synthetic non-resorbable silicon-containing calcium phosphate biomaterial having a microporosity set to 17.5% by volume or greater and a surface free energy set to 19 mJ/m² or greater; and (b) configuring said osteoinductive biomaterial as a replacement bone-material for osteoinduction.

DETAILED DESCRIPTION OF THE INVENTION

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The inventors have recognised the advantage for patients of providing an osteoinductive biomaterial over a purely osteoconductive biomaterial.

Some known scaffold materials rely on the dissolution of the scaffold to provide osteoinductivity and, as a result, must dissolve under biological conditions in order to provide osteoinduction. The inventors have recognised that the dissolution of a scaffold into the body can occur in part or in whole prior to effective bone formation. Furthermore, the inventors have found that the dissolution products of a scaffold can potentially impede or reduce the rate of bone formation as the local biochemical environment becomes saturated with high concentrations of foreign ionic species or as particulate debris generated during dissolution elicits an inflammatory response.

The inventors have found that these drawbacks to resorbable materials can result in low and inconsistent levels of bone formation. This inconsistency has also made in vivo validation of the principle of using a material with intrinsic osteoinductive properties difficult.

The inventors have also recognised the potential disadvantage of providing a partially resorbable material comprising both non-resorbable parts and resorbable parts. For example, as described in US 2007/0218098, particles of low solubility contained in a material of high solubility can be carried off by phagocytes and deposited in the body's lymphatic system.

The inventors have then surprisingly found a biomaterial that is osteoinductive but whose osteoinductive behaviour does not depend on the resorption of its scaffold in vivo. On the contrary, the osteoinductive biomaterial of the present invention is effective at least in part because of its low rate of resorption in vivo. In particular, the inventors have found that the combination of the use of a calcium phosphate material, the processing of this calcium phosphate material into a material having a microporosity of at least 17.5% by volume (more beneficially at least 23% by volume) and the modification of the surface energy of the calcium phosphate by inclusion of silicon provides an advantageous osteoinductive material.

Accordingly, the biomaterial of the present invention may be described as an osteoinductive biomaterial.

Figure 1:
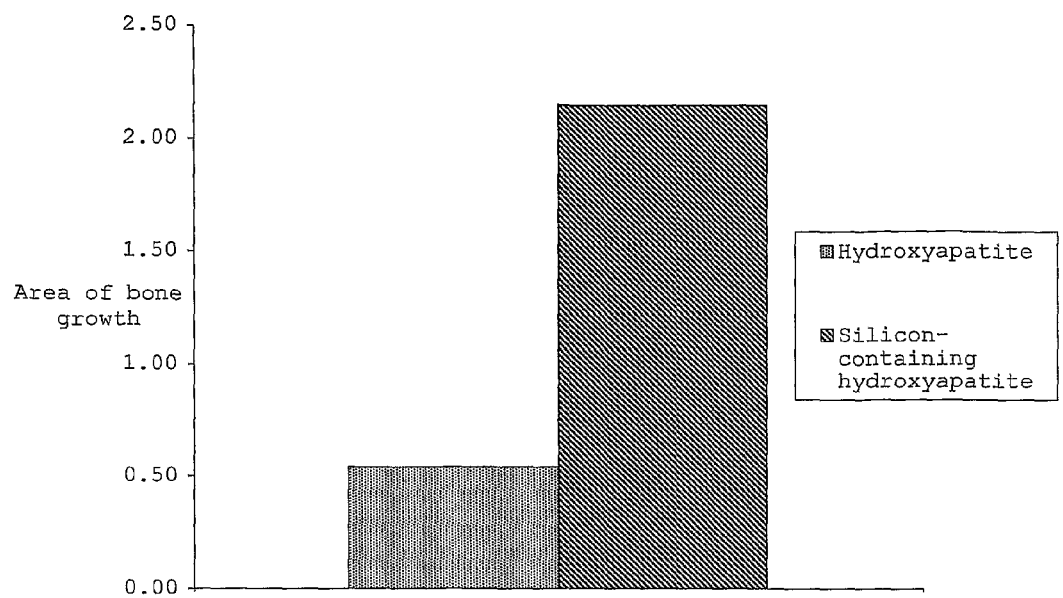
FIGS. 1 and 2 show examples of the present invention.
Figure 2:
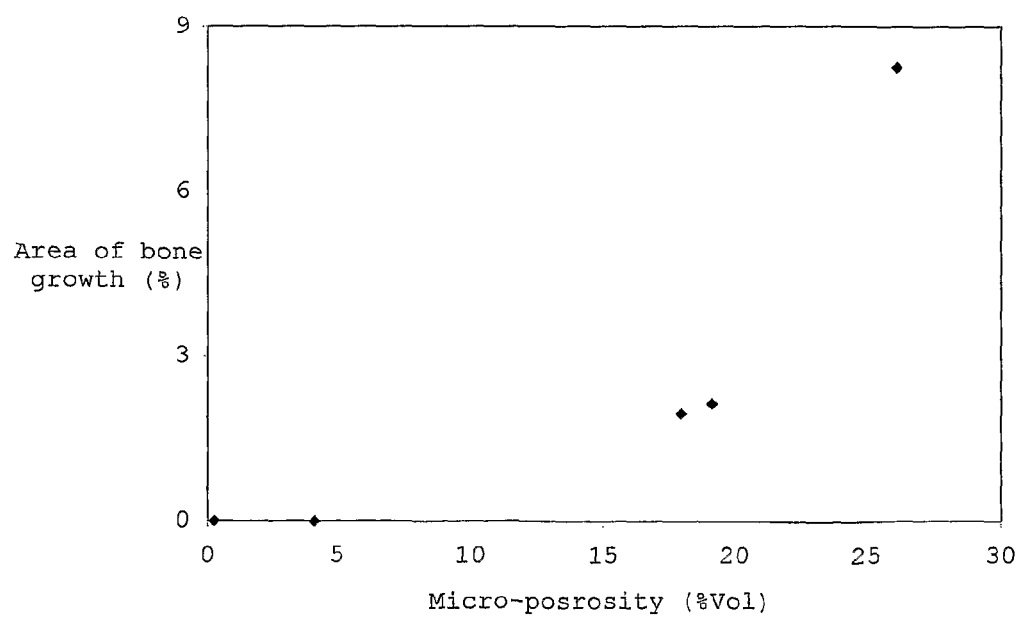

The combined effects of porosity and silicon-inclusion in the calcium phosphate material are shown in the examples. In particular, FIG. 1 shows that the surface energy of a calcium phosphate material can be modified by including silicon in the material to increase the osteoinductive effect of the material. It is noted that the microporosity of the two examples shown in FIG. 1 is approximately the same. In addition, FIG. 2 shows the effect of osteoinduction of increasing the microporosity of a silicon-containing calcium phosphate material.

A biomaterial is a material that is suitable for use in vivo. A biomaterial can be described as being biocompatible, meaning that, according to ISO 10993, the material performs, replaces or augments biological function. The biomaterial may be a replacement bone material. For example, it may be used as a synthetic bone material, including dental materials, for example for use in bone substitution, implants, fillers and cements, coatings for metallic implants and for making hydroxyapatite-polymer composites.

Porosity of the biomaterial (in particular the range of interconnection diameters) is measured by mercury intrusion porosimetry. In particular, the following conditions are typically used for this measurement: an advancing contact angle of 140 degrees, a liquid-vapour interfacial free energy for mercury of 0.480 mJ/m², and a mercury density of 13.5335 g/ml. The measurement is carried out at ambient temperature and pressure (20° C. and 1 atmosphere). The total pore volume within a range of interconnection diameters may be measured by mercury intrusion porosimetry volume fraction measurement of pores.

As used herein, the term "microporosity" refers to the porosity resulting from micropores. Micropores are those pores measured by mercury intrusion porosimetry analysis to have an interconnection diameter of 50 nm to 10 µm. While only some of the interconnections between neighbouring may be circular, the term interconnection diameter refers to the equivalent circular diameter of the pores as measured by mercury intrusion porosimetry.

The microporosity of the porous body of the present invention is at least 17.5% by volume, more beneficially at least 23% by volume. The inventors have found that below these levels of microporosity, the rate of osteoinduction is reduced. The microporosity may be 19% by volume or more, for example 20% by volume or more, such as 24% by volume or more, for example 25% by volume or more, such as 30% by volume or more, for example 35% by volume or more. The microporosity may be 60% by volume or less, for example 55% by volume or less or 50% by volume or less, such as 40% by volume or less, for example 35% by volume or less, such as 30% by volume or less. In an illustrative example, the microporosity may be preferably 23 to 60% by volume, for example 23% to 50% by volume or 30% to 50% by volume, such as 23% to 40% by volume, for example 25 to 35% by volume, for example about 26% by volume. In particular, the inventors have found osteoinduction to increase with the microporosity. However, the inventors have found that a maximum level of microporosity is preferable so that pores do not coalesce, thereby possibly reducing the capillary pressure of the biomaterial.

If the biomaterial contains pores other than the micropores as discussed later (e.g. macropores), the microporosity satisfies the following relationship:

$$V_m \geq 0.175(V_T - V_O)$$

where $V_T$ is the total volume of the biomaterial, $V_S$ is the total volume of the micropores and $V_O$ is the total volume of the pores other than the micropores. If there is no other porosity than the microporosity, then $V_O=0$.

Preferably, at least 90% by number of the pores having an interconnect diameter of less than 10 μm have an interconnect diameter of 50 nm to 10 μm; more preferably, at least 90% by number of the pores having an interconnect diameter of less than 10 μm have an interconnect diameter of 0.1 to 8 μm; still more preferably, at least 90% by number of the micropores having an interconnect diameter of less than 10 μm have an interconnect diameter of 0.1 to 5 μm. Working within these ranges is thought to increase the osteoinductive properties of the biomaterial. Thus, while the porous body may have some pores having an interconnection diameter less than that of the micropores, these pores are not thought to contribute to the osteoinductive properties of the porous body. Therefore, preferably the body does not contain a significant number of pores (i.e. substantially no pores) having an interconnection diameter of less than 50 nm. Preferably, these numbers of pores having these specific ranges of interconnect diameter are 95% by number, more preferably 98% by number, and more preferably 99% by number.

The microporosity preferably comprises an open porous network. This is thought to favour a high permeability and wicking capacity. Thus, the micropores preferably have an interconnect level of 90% or greater, more preferably 96% or greater, and even more preferably 99% or greater. The interconnection level (vol/vol %) is measured by Helium Pyconometry measurement and a theoretical density for the same material.

Preferably, the mean interconnect diameter of the micropores (i.e. of the pores having a mean interconnect diameter of between 50 nm and 10 μm) is 0.5 μm or more. The mean interconnect diameter is measured by obtaining a plot of pore size distribution (i.e. of pores size vs. number of pores having this pore size) using mercury intrusion porosimetry and then calculating the mean of the results by adding up the results and dividing by the integrated area of the plot. For example, the mean interconnect diameter may be 0.7 μm or more, such as 0.8 μm or more, 0.813 μm or more, 0.9 μm or more, or 0.94 μm or more, such as 1.0 μm or more, for example 1.1 μm or more, or 1.25 μm or more, such as 1.3 μm or more. Preferably, the mean interconnect diameter is 2.0 μm or less, such as 1.8 μm or less, for example 1.7 μm or less, such as 1.6 μm or less, for example 1.5 μm or less, for example 1.4 μm or less. To take an exemplary embodiment, the mean interconnection diameter of the pores may be 0.75 μm to 1.8 μm, for example, 0.813 μm to 1.7 μm, such as 1.0 to 1.5 μm, for example 1.3 μm to 1.4 μm, such as about 1.3 μm. The inventors have found the upper limits of mean interconnection diameter can result in an advantageous permeability to allow biological fluid to flow through the biomaterial, but that a larger mean interconnection diameter can contribute to a low capillary pressure. The inventors have also found the lower limits of mean interconnection diameter can result in an advantageous capillary pressure difference to increase the driving force of the up-take of biological fluids into the biomaterial, but that a lower mean interconnection diameter can contribute to a low permeability. Accordingly, the minimum and maximum mean interconnection diameters may be chosen to provide the preferred permeability resulting from the micropores and the preferred capillary pressure difference in water described herein, for example a permeability of 0.206 $m^2$ or greater and a capillary pressure difference of 3.7 kPa or more.

The biomaterial of the present invention is chemically stable. As used herein, the term "non-resorbable" is used to refer to a chemically stabile biomaterial. The term is defined to refer to a non-soluble material. Specifically, the material shows no significant structural dissolution when it is immersed in water. Since resorption may be dependent on porosity, in order to compare the resorption of different materials, the level of resorption is measured for the bulk material and on samples having the same surface area.

Thus, while others have attempted to promote bone growth by releasing certain trace elements, the inventors have recognised the disadvantages of relying on the resorbable characteristics of a biomaterial to promote bone growth. By providing a non-resorbable material, the unpredictable effects which depend on both the biomaterial and the local environment into which the biomaterial is implanted are avoided.

Accordingly, the present invention provides a non-resorbable scaffold for bone material which reliably and reproducibly induces significant levels of bone formation when tested in ectopic sites in preclinical models. Such bone formation is intimately associated with the scaffold itself, rather than being associated with either cytokines or dissolution products provided or associated with the scaffold. This allows accelerated bone formation to occur only where the scaffold is implanted, rather than at random wherever circulatory fluids transport adsorbed cytokines or dissolution products.

Non-resorbable calcium phosphate materials are well known in the art. Calcium phosphates contain both calcium ($Ca^{2+}$) and phosphate ($PO_4^{3-}$). Although a formal charge is given to these two units, it is understood that this is for illustrative purposes only and that, within the lattice of calcium phosphate, the formal charge on each unit may be different or, for example, the phosphate may be protonated. Preferably, the calcium to phosphorus molar ratio is between 1:1.1 and 2.0, for example 1:1.5 to 1:2.0, such as 1:1.6 to 1:1.7, for example about 1:1.67.

Examples of preferred non-resorbable calcium phosphate material are hydroxyapatite materials. Hydroxyapatite materials are well known in the art. Hydroxyapatite itself has the chemical formula $Ca_{10}(PO_4)(OH)_2$, i.e. with a calcium/phosphorus ratio of 1.67. Hydroxyapatite materials may also comprise substituted hydroxyapatite. For example, sodium, magnesium, aluminium, iron, copper, barium, strontium and/or carbonate may be substituted into the hydroxyapatite. Non-resorbable hydroxyapatite materials may also comprise one or more hydroxyapatite phases and one or more phases of other non-resorbable materials.

In the silicon-containing calcium phosphate materials of the present invention, silicon is contained in the crystal lattice of the calcium phosphate. Thus, the silicon is contained in the non-resorbable calcium phosphate phase. In a preferred embodiment, the silicon is actually substituted into the crystal lattice. The substitution may occur in the place of phosphorus, taking due account of the different valency of silicon and phosphorus. As a result of the actual substitution of the silicon into the crystal lattice, the silicon is thought to become less readily resorbed than if the silicon was merely added to the crystal lattice, thereby remaining unsubstituted in the lattice. The substitution of the silicon into the crystal lattice may be measured, for example, by the techniques described in EP 0951441. For example, the substitution of silicon actually into the lattice of the calcium phosphate material may be observed by an increase in the lattice parameters measured by X-ray diffraction.

Preferably, the calcium phosphate material of the present invention has substantially no impurity phases that are resorbable. In particular, the calcium phosphate material of the present invention preferably has substantially no impurity phases of calcium oxide and/or tricalcium phosphate. The inventors have recognised that these two impurity phases may be resorbable (see for example *J. Eur. Ceramic Society* 23, 1039-1045 (2003) for tricalcium phosphate). Thus, preferably the material contains 90% or more of one or more non-resorbable phases (e.g. less than 10% of, for example, tricalcium phosphate, such as less than 5%, for example less than 2%, such as less than 1%), preferably 95% or more, more preferably 98% or more, such as 99% or more, for example about 100% (as measured by X-ray diffraction). In other words, preferably all of the material is non-resorbable, disregarding inevitable impurities.

Reflecting the lack of any substantial impurity phases that are resorbable, preferably the phase purity of the non-resorbable calcium phosphate material, as measured by X-ray diffraction, is 90% or greater. More preferably, the phase purity of the calcium phosphate material is 95% or greater, more preferably 98% or greater, such as 99% or greater, for example about 100%. As such, the material is preferably essentially a single phase pure material, together with unavoidable impurities.

The inventors have found that the surface free energy of the calcium phosphate material can be modified by adding silicon to it. In particular, the inventors have found that surface free energy increases with the amount of silicon added to the calcium phosphate materials. The inventors have further found that osteoinductivity increases with surface free energy when combined with the other factors described herein.

Accordingly, preferably silicon is contained in the calcium phosphate crystal lattice in an amount that the calcium phosphate material has a surface free energy of 19 $mJ/m^2$ or greater.

The surface free energy, $mJ/m^2$, is measured using Kruss Drop Analysis of contact angles for liquids (e.g. water) with a known liquid-vapour interfacial free energy on fully-dense surfaces of the same material chemistry.

Preferably, the silicon modifies the surface free energy to 20 $mJ/m^2$ or greater, for example 30 $mJ/m^2$ or greater, such as 35 $mJ/m^2$ or greater, for example 40 $mJ/m^2$ or greater, such as 50 $mJ/m^2$ or greater. Preferably, the maximum free energy is 57 $mJ/m^2$, for example 50 $mJ/m^2$, such as 45 $mJ/m^2$. Illustrative examples of preferred ranges of surface free energy are 30 to 57 $mJ/m^2$, such as 40 to 57 $mJ/m^2$; more preferably from 35 to 50 $mJ/m^2$; even more preferably from 35 to 45 $mJ/m^2$. While the inventors have found osteoinductive behaviour to increase with surface free energy, the inventors have found that the surface properties of the biomaterial can change as the surface free energy approaches 57 $mJ/m^2$.

For one particular example, silicon-substituted hydroxyapatites, the inventors have found silicon to be especially versatile in modifying the surface free energy of the material.

Other techniques known in the art may also be used to further modify the surface free energy of the surface as well as silicon substitution. For example, the surface free energy of a substrate may be controlled by varying chemical composition, nanoscale texture, doping, substitutions, contamination, or subjecting the material to heat or chemical treatments.

Preferably, silicon is into the calcium phosphate crystal lattice in an amount of 0.1 to 5.0 weight %. More preferably, it is substituted in an amount of 0.5 to 1.6 weight %, such as 0.5 to 1.0 weight %, for examples about 0.8 weight %. If substituted into the crystal lattice, the silicon may exist in the form of, for example, a silicon ion or a silicate ion. The inventors have found that the combination of the microporosity with these ranges of silicon content may result in enhanced osteoinduction.

A suitable method of forming a silicon-substituted hydroxyapatite material in which silicon is substituted into the crystal lattice and which has substantially no impurity phases of calcium oxide and/or tricalcium phosphate, and having a phase purity, as measured by X-ray diffraction, of at least 98%, is described in EP 0951441, the contents of which are incorporated herein by reference.

For the avoidance of doubt, the term silicon-substituted as used herein also encompasses silicate-substituted. Likewise, silicate-substituted as used herein also encompasses silicon-substituted.

Preferably, the calcium phosphate material of the present invention is a sintered material. If the material has not been sintered but is, for example, derived from a source such as coral, it may be resorbable (such as that described in US 2004/0078087). Sintering is well-known in the art as a process of heating resulting in the coalescence of individual particles. This coalescence of particles can contribute to the non-resorbable nature of the resulting material.

For calcium phosphate materials, the temperature of sintering depends on the material itself. Typically, sintering may be carried out at a temperature of anywhere in the region of 500 to 1400° C., for example 900 to 1250° C., such as about 1200° C. Sintering may be carried out for, for example between 20 minutes and 24 hours, such as between 1 hour and 12 hours, for example about 4 hours. Sintering may be carried out, for example, under nitrogen.

The biomaterial of the present invention may comprise macropores. As used herein, the term "macropores" refers to pores having a mean interconnection diameter of more than 10 µm. While not required, this network of large pores is thought to facilitate the transport of circulatory and biological fluids within the biomaterial. This can increase the rate at which biological fluids and proteins are absorbed into the small pores (micropores) and adsorbed onto the surfaces of the biomaterial. Preferably, at least 90% of the macropores (more preferably, 95%, even more preferably 98%) of the large pores (macropores) have an interconnect diameter of 50 µm or more.

Preferably, the macroporosity (i.e. the porosity resulting from the macropores) is 20% by volume or greater, for example 30% or greater, such as 40% or greater. The macroporosity may be 70% or less, for example 60% or less, such as 50% or less. In one exemplary embodiment, the macroporosity is preferably 20% to 60% by volume. Within these limits, the beneficial effect of circulating biological fluids and proteins to the micropores may be increased.

Preferably, if the body contains both macropores and micropores, the overall porosity of the body of the present invention is preferably, as measured by archimedes density measurement using water, 45% by volume or greater, such as 50% by volume or greater, for example 60% by volume or greater, such as 70% by volume or greater. The inventors have found that these lower limits can contribute to a beneficial osteoinductive effect. Preferably, the overall porosity is 95% by volume or less, such as 90% by volume or less, for example 85% by volume or less. The inventors have found that, above these upper limits, coalescence of pores may occur resulting in reduced benefit from osteoinduction. Thus, an illustrative example of a preferred range of overall porosity is 50% to 90% by volume.

Without wishing to be bound by theory, the microporosity of the material of the present invention is thought to allow the porous body to possess a high capillary action to adsorb liquids from biological fluid. The high capillary action may result in a high concentration of the bone growth-promoting proteins naturally present in the biological fluid in a confined environment. In addition, the inclusion of silicon in the calcium phosphate material is thought to provide a surface environment that is conducive to the attachment and absorption of bone-growth promoting proteins and facilitates the capillary action of the body. The up-take of biological fluids and proteins by the porous body resulting from the combination of these two factors may contribute to the osteoinductive properties of the biomaterial.

Accordingly, preferably the permeability of the biomaterial of the present invention through the micro-scale interconnected porosity (i.e. resulting from the micropores) of 0.206 nm$^2$ or greater.

The permeability (nm$^2$) depends on the distribution of the interconnection diameters of the pores and may be determined by mercury intrusion porosimetry. From the results of the mercury intrusion porosimetry, the permeability is then determined as follows:

$$K = \frac{\Phi d_P^2}{32}$$

where K is the permeability resulting from the micropores; and $d_P$ is the mean interconnection diameter of the micropore interconnections as calculated from the mercury intrusion porosimetry measurement of the interconnect size. $\Phi$ is the volume fraction of pores filled with mercury.

Preferably, the permeability is 0.8 nm$^2$ or more; more preferably, it is 1.0 nm$^2$ or more. The permeability may be 10 nm$^2$ or less, such as 5 nm$^2$ or less, for example 3 nm$^2$ or less. For example, in one embodiment, the permeability may be 0.8 nm$^2$ to 5 nm$^2$. The inventors have found bone growth to be beneficially achieved within these limits.

Preferably, in order to encourage the absorption of bone growth-promoting factors from biological fluids into the biomaterial, the capillary pressure difference of the material may be 3.7 kPa or more when measured in water. The capillary pressure difference is measured in water (e.g. ultra pure water) and determined from the following relationship between the surface free energy and the interconnection diameter:

$$\Delta P = 2\gamma_{LV}\cos(\theta)/r$$

where $\Delta P$ is the Capillary Pressure Difference, $\gamma_{LV}$ (mJ/m$^2$) is the liquid-vapour interfacial free energy of the liquid in contact with the same material, $\theta$ is the contact angle of the liquid on the same material, and r (in m) is the mean interconnection diameter of the micropores measured by mercury porosimetry.

In this equation, the liquid-vapour interfacial free energy can be determined by the Young's equation, which describes the energies at the boundary between liquid, vapour and solid when a drop of liquid (e.g. water) forms on the surface of material:

$$\gamma_{SV} = \gamma_{LV}\cos\theta + \lambda_{SL}$$

Here, $\gamma_{SV}$ is the solid-vapour interfacial energy (measured in mJ/m$^2$), $\theta$ is the contact angle and $\lambda_{SL}$ is the solid-liquid interfacial energy. All interfacial measurements are made using the Kruss drop analysis technique described herein.

Preferably, the capillary pressure difference is 3.9 kPa or above such as 3.97 kPa or above, such as 15 kPa or greater, for example 25 kPa or above, or 36 kPa or above, such as 40 kPa or above, more preferably, it is 50 kPa or above. The capillary pressure difference may be 150 kPa or less, such as 100 kPa or less, for example 85 kPa or less, such as 70 kPa or less. Thus, in one illustrative example, the capillary pressure difference of the biomaterial is preferably 3.7 kPa to 100 kPa, such as 20 kPa to 100 kPa. The inventors have found bone growth to be beneficially achieved within these limits.

Preferably, in order to allow the rapid transport of circulatory and biological fluids within the biomaterial and allow advantageous build-up of bone growth-promoting materials absorbed from a biological medium, the biomaterial preferably has a total wicking capacity (vol/vol %) of 400% by volume or more. (Both the micropores and optional macropores contribute to the total wicking capacity). The total wicking capacity may be controlled by varying the total pore volume of the biomaterial (both micro- and macropores) and the interconnection level of the pores in the biomaterial.

The total wicking capacity (vol/vol %) of a single material over the entire pore size range is derived from an Archimedes density measurement using water. Water is used rather than a biological medium such as blood in order to increase the reproducibility of the measurement.

Preferably, the total wicking capacity is 420% by weight or greater; more preferably, it is 430% by weight or greater. The wicking capacity may be 800% by weight or less, such as 600% by weight or less, for example 500% by weight or less.

In one illustrative example, the total wicking capacity may be preferably 400% to 600%, for example 420 to 500%. The inventors have found bone growth to be beneficially achieved within these limits.

Preferably, the total wicking capacity attributed to the micropores may be maximized. The wicking capacity of the micropores is affected by the permeability of the micropores and the capillary pressure difference. However, in order to maintain the structural benefits of the scaffold, an upper limit may be placed on the wicking capacity.

The synthetic biomaterial described herein may be used in medicine. In particular, it may be used in therapy or surgery. In one embodiment, it is used as a bone-replacement material.

Accordingly, the biomaterial may be used, for example, to treat bone fractures, achieve spinal fusions or to repair bone tumors or vertebral compression fractures. In these uses, the biomaterial is implanted into a patient or animal. This may be achieved using techniques known in the art. The present invention also provides for a synthetic bone material, bone implant, orthopaedic implant, tissue implant, bone graft, bone substitute, bone scaffold, filler, coating or cement comprising a composition as herein described. The present invention also provides for the use of the compositions as herein described in these applications. The present invention also provides for a method of treating a patient, the method comprising delivering a bioceramic composition as herein described to a site in the patient to be treated. The present invention also provides a bioceramic composition as herein described for use as a biomedical implant. The present invention also provides a bioceramic composition as herein described for use in therapy. The present invention also provides a bioceramic composition as herein described for use in reconstructive or replacement surgery.

It will be appreciated that bioceramic composition as herein described may be used in these biomedical applications on its own or in conjunction with one or more of a biocompatible polymer, other type of ceramic, glass, and/or glass-ceramic material.

The biomaterial may be provided in any known form, for example as dry granules, as a paste with a solvent (e.g. water or blood), in a binder or as a solid pre-formed, pre-shaped implant.

The present invention further provides a method of selecting a synthetic porous osteoinductive biomaterial and providing osteoinduction of bone, the method comprising: (a) selecting an osteoinductive synthetic non-resorbable silicon-containing calcium phosphate biomaterial having a microporosity set to 17.5% by volume or greater and a surface free energy set to 19 mJ/m² or greater; and (b) configuring said osteoinductive biomaterial as a replacement bone-material for osteoinduction.

The present invention further provides the use of silicon, a surface free energy of 19 mJ/m² and a microporosity of 17.5% by volume or greater (more beneficially 23% by volume or greater) to impart osteoinductive properties to a synthetic non-resorbable calcium phosphate biomaterial. Osteinductive properties refer to the inherent ability of a biomaterial to exhibit osteoinduction.

All measurements described herein are made at room temperature (20° C.) and atmospheric pressure (1 atmosphere) unless stated otherwise.

EXAMPLES

Several samples were prepared from material synthesised according to the method described in EP 0951441. The material was then processed into a porous biomaterial according to the present invention using the foaming method described in WO0020353. The entire contents of WO0020353 are incorporated herein by reference. Using this technique, pore size and porosity was controlled to achieve the desired pore sizes and porosities by varying the relative proportions of the ingredients within the ceramic slip, the physical characteristics of the ceramic particulate, the amount of milling media added during mill-foaming and, additionally by the sintering procedure.

These samples were then implanted in an animal and their osteoinductivity was measured. Results are shown in Table 1. To measure the osteoinductivity of the samples, the calcium phosphate biomaterials were implanted into the right and left sacrospinalis muscle of skeletally mature female commercially cross bred sheep aging greater than two years and weighing between 65 and 80 kg. Animals were euthanized at week 12. After sacrifice, implants surrounded by a layer of muscle were removed and fixed for histology. Radiography was carried out to locate the implants in the muscle. Thin sections of ~70 μm thick were prepared by ultramicrotomy in a proximal distal direction. Image analysis and histomorphometry was carried out on thin sections to assess bone formation within the implants. Percentage of bone area, soft tissue area and the area occupied by the test material were calculated. In addition percentage of the amount of bone attached to the calcium phosphate surfaces was measured. Scanning Electron Microscopy (SEM) and EDAX were also carried out to evaluate the quality of bone formation and the elements present within the implants.

| Ex. | Material | Surface free energy (mJ/m²) | Microporosity (% Vol) | Mean interconnection diameter (μm) | Capillary pressure difference (kPa) | Permeability (nm²) | Bone Area (%) |
|---|---|---|---|---|---|---|---|
| 1 | SiHA | 38.31 | 0.9 | 1.743 | 37.8 | 2.161 | 0.00 |
| 2 | SiHA | 38.31 | 4.1 | 0.9436 | 69.8 | 0.206 | 0.00 |
| 3 | SiHA | 38.31 | 18.2 | 1.817 | 36.2 | 2.419 | 1.96 |
| 4 | SiHA | 38.31 | 20.0 | 0.7989 | 82.4 | 0.075 | 2.15 |
| 5 | SiHA | 38.31 | 26.4 | 1.347 | 48.9 | 1.158 | 8.26 |
| C1 | HA | 19.49 | 19.7 | 1.075 | 4.7 | 0.586 | 0.54 |
| C2 | HA | 19.49 | 16.8 | 0.9844 | 5.2 | 0.883 | 0.57 |
| C3 | HA | 19.49 | 21.3 | 1.368 | 3.7 | 1.343 | 0.86 |

SiHA = silicon-substituted hydroxyapatite (0.8 wt % silicon was used in examples 1 to 5).
C1 to C3 are comparative examples of hydroxyapatite (non-containing silicon).

Some of these results are illustrated in FIGS. 1 and 2.

The invention claimed is:

1. A synthetic non-resorbable silicon-containing calcium phosphate biomaterial having a microporosity of 25-35% by volume, wherein the surface free energy of the biomaterial is 30 mJ/m² or greater, and wherein micro-pores resulting in the microporosity have an interconnection diameter of 50 nm to 10 μm as measured by mercury porosimetry analysis, wherein the mean interconnected diameter of micro-pores resulting in the microporosity is 0.5 μm to 10 μm.

2. The silicon-containing calcium phosphate biomaterial of claim 1, wherein the calcium phosphate biomaterial comprises a hydroxyapatite material.

3. The silicon-containing calcium phosphate biomaterial of claim 1, wherein the silicon is substituted into the crystal lattice of the calcium phosphate material.

4. The silicon-containing calcium phosphate biomaterial of claim 1, wherein the calcium phosphate forming the calcium phosphate material has substantially no impurity phases of calcium oxide and/or tricalcium phosphate.

5. The silicon-containing calcium phosphate biomaterial of claim 1, wherein the calcium phosphate forming the calcium phosphate material has a phase purity, as measured by X-ray diffraction, of at least 90%.

6. The silicon-containing calcium phosphate biomaterial of claim 1 containing from 0.1% to 1.6% by weight of silicon.

7. The silicon-containing calcium phosphate biomaterial of claim 1, wherein the material has a permeability resulting from the microporosity of 0.206 nm² or greater.

8. The silicon-containing calcium phosphate biomaterial of claim 1, wherein the material has a capillary pressure in water of 3.7 kPa or greater.

9. The silicon-containing calcium phosphate biomaterial of claim 1, wherein the surface free energy of the material is 35 mJ/m² or greater.

10. The silicon-containing calcium phosphate biomaterial of claim 1, wherein the material also contains macro-pores.

11. The biomaterial of claim 1, wherein the total wicking capacity (vol/vol %) of the biomaterial is 400% by volume or more.

12. A silicon-containing sintered calcium phosphate biomaterial having a microporosity of 25-35% by volume and a surface free energy of 30 mJ/m² or greater, wherein micro-pores resulting in the microporosity have an interconnection diameter of 50 nm to 10 μm as measured by mercury porosimetry analysis, wherein the mean interconnected diameter of micro-pores resulting in the microporosity is 0.5 μm to 10 μm.

13. A synthetic silicon-substituted calcium phosphate biomaterial having a microporosity of 25-35% by volume and a surface free energy of 30 mJ/m² or greater, wherein the biomaterial comprises substantially no impurity phases of calcium oxide and/or tricalcium phosphate, wherein micropores resulting in the microporosity have an interconnection diameter of 50 nm to 10 μm as measured by mercury porosimetry analysis, wherein the mean interconnected diameter of micropores resulting in the microporosity is 0.5 μm to 10 μm.

14. A synthetic calcium phosphate biomaterial as defined in claim 1 for use in medicine.

15. A method of treating bone fractures, achieving spinal fusions, repairing bone tumours or vertebral compression fractures, the method comprising implanting a biomaterial according to claim 1 in a patient or animal.

16. A method of selecting a synthetic porous osteoinductive biomaterial and providing osteoinduction of bone to treat a patient or animal, the method comprising:

(a) selecting an osteoinductive synthetic non-resorbable silicon-containing calcium phosphate biomaterial having a microporosity of 25-35% by volume, a surface free energy of 30 mJ/m$^2$ or greater and micropores resulting in the microporosity have an interconnection diameter of 50 nm to 10 μm as measured by mercury porosimetry analysis, wherein the mean interconnected diameter of micropores resulting in the microporosity is 0.5 μm to 10 μm;

(b) configuring said osteoinductive biomaterial as a replacement bone-material to provide for osteoinduction; and (c) implanting said osteoinductive biomaterial in the patient or animal.

* * * * *

UNITED STATES PATENT AND TRADEMARK OFFICE
CERTIFICATE OF CORRECTION

PATENT NO. : 8,999,366 B2
APPLICATION NO. : 12/865573
DATED : April 7, 2015
INVENTOR(S) : Thomas Buckland Page 1 of 1

It is certified that error appears in the above-identified patent and that said Letters Patent is hereby corrected as shown below:

On the title page, under item (65), please insert item (30) so that it reads:

--(30)    Foreign Application Priority Data

February 1, 2008   (GB) ................................. 0801935.8--

Signed and Sealed this
Twenty-eighth Day of July, 2015

Michelle K. Lee
*Director of the United States Patent and Trademark Office*